US012471954B2

(12) United States Patent
Jeon et al.

(10) Patent No.: US 12,471,954 B2
(45) Date of Patent: Nov. 18, 2025

(54) HANDHELD SKIN TREATMENT DEVICE

(71) Applicant: Access Business Group International LLC, Ada, MI (US)

(72) Inventors: Soha Jeon, Seoul (KR); Jaehyeon Joo, Seoul (KR)

(73) Assignee: Access Business Group International LLC, Ada, MI (US)

( * ) Notice: Subject to any disclaimer, the term of this patent is extended or adjusted under 35 U.S.C. 154(b) by 325 days.

(21) Appl. No.: 18/115,078

(22) Filed: Feb. 28, 2023

(65) Prior Publication Data

US 2024/0285313 A1 Aug. 29, 2024

(51) Int. Cl.
*A61B 17/54* (2006.01)
*A61N 5/06* (2006.01)

(52) U.S. Cl.
CPC .......... *A61B 17/545* (2013.01); *A61N 5/0616* (2013.01); *A61N 2005/0663* (2013.01)

(58) Field of Classification Search
CPC .................. A61B 17/545; A61B 17/54; A61B 2017/00747; A61B 2017/00761; A61B 2017/320004; A61B 2217/005; A61M 35/003; A61M 2037/0007; A61H 9/0028; A61H 2201/10; A61H 2201/105; A61H 2201/1685; A61H 15/02; A61H 7/005; A61N 5/0616; A61N 2005/0659; A61N 2005/0663
See application file for complete search history.

(56) References Cited

U.S. PATENT DOCUMENTS

| | | | | |
|---|---|---|---|---|
| 6,673,082 | B2 | 1/2004 | Mallett et al. | |
| 6,923,762 | B1 * | 8/2005 | Creaghan, Jr. | A61B 5/489 600/249 |
| 6,942,649 | B2 | 9/2005 | Ignon et al. | |
| 9,775,646 | B2 | 10/2017 | Shadduck | |
| D807,141 | S | 1/2018 | Juranitch et al. | |
| 9,902,047 | B1 | 2/2018 | Juranitch et al. | |
| 10,252,051 | B2 | 4/2019 | Nichols | |

(Continued)

FOREIGN PATENT DOCUMENTS

| | | | |
|---|---|---|---|
| KR | 20220023876 | 3/2022 | |
| WO | WO-2022229403 A1 * | 11/2022 | A24F 40/05 |

*Primary Examiner* — Diane D Yabut
(74) *Attorney, Agent, or Firm* — Warner Norcross + Judd LLP

(57) ABSTRACT

A skin treatment device configured to selectively operate in hydradermabrasion mode and in massage mode. The skin treatment device includes a working end and a plurality of interchangeable working attachments that can be selectively mounted to the working end. The working attachments includes at least one hydradermabrasion tip and at least one massage head. The device includes a liquid delivery system for moving liquid from a supply canister to the working attachment and from the working attachment to the waste receptacle. The hydradermabrasion tip includes a supply aperture for delivering liquid to the target region of skin and a return aperture for returning liquid from the target region to the waste receptacle. The device may include a red-light therapy system for delivering red-light therapy to a target region. The red-light therapy system may include a plurality of red LEDs positioned to emit red light through an installed working attachment.

24 Claims, 12 Drawing Sheets

(56) References Cited

U.S. PATENT DOCUMENTS

| | | | | |
|---|---|---|---|---|
| 10,399,208 | B1 | 9/2019 | Juranitch | |
| 10,661,406 | B2 | 5/2020 | Graves et al. | |
| 11,446,477 | B2 | 9/2022 | Ignon et al. | |
| 2003/0120129 | A1 * | 6/2003 | Nakamura | A61B 1/0676 600/101 |
| 2004/0097967 | A1 | 5/2004 | Ignon | |
| 2006/0253125 | A1 | 11/2006 | Ignon | |
| 2007/0105065 | A1 * | 5/2007 | Snyder | A61C 17/02 604/77 |
| 2008/0119913 | A1 * | 5/2008 | Powell | A61N 5/0616 606/9 |
| 2013/0158547 | A1 * | 6/2013 | David | A61B 17/54 606/41 |
| 2021/0085367 | A1 | 3/2021 | Shadduck et al. | |
| 2021/0353922 | A1 | 11/2021 | Ignon et al. | |
| 2022/0054810 | A1 * | 2/2022 | Lee | A45D 34/04 |
| 2022/0151861 | A1 | 5/2022 | Ignon et al. | |
| 2022/0211988 | A1 | 7/2022 | Ignon et al. | |
| 2023/0013440 | A1 | 1/2023 | El-Sherif et al. | |

* cited by examiner

HANDHELD SKIN TREATMENT DEVICE

BACKGROUND OF THE INVENTION

The present invention relates to devices for treating skin, and more particularly to devices that perform hydradermabrasion, massage and red-light therapy.

There is a growing demand for skin treatment, such as skin resurfacing and rejuvenating procedures. As a result of this demand, various technologies have been developed to implement these procedures. For example, microdermabrasion has become an increasingly popular method for treating skin through a relatively aggressive abrasive procedure. More specifically, microdermabrasion generally includes the process of spraying microcrystals on the surface of skin to exfoliate the skin and slough off dull, surface-level skin cells. Typical microdermabrasion treatment devices have the potential to cause harm if not operated properly and, as a result, are primarily operated by skilled clinicians in clinical settings.

Given the generally aggressive nature of microdermabrasion, other technologies have been developed to assist in the exfoliation and cleaning of skin. For example, one alternative to microdermabrasion is hydradermabrasion (or hydrodermabrasion). Hydradermabrasion differs from microdermabrasion in that it involves the application of a jet of liquid onto the skin rather than a spray of aggressive microcrystals. The jet of liquid, such as water, saline solution or other liquids, is sprayed against the skin to mechanically slough off or peel the outer surface of the skin. The dead skin cells and other debris are carried away from the skin with the waste liquid. Although many hydradermabrasion devices are designed for use in a clinical setting, there are a number of commercially available skin treatment devices intended for home use. For example, a number of existing devices are available on the market that make it possible to direct a jet of liquid against the surface of the skin with sufficient force for the liquid to mechanically remove dead skill cells and other debris from the skin while simultaneously applying a vacuum that draws away the waste liquid and the dead skin cells and other debris produced in the process. Conventional home devices allow a consumer to exfoliate, clean and potentially hydrate the skin. Typical home devices are designed primarily for use on the face and neck, but can be suitable for use on other regions of the skin. Commercially-available home-use hydradermabrasion devices represent an improvement over clinical systems in that they allow a consumer to obtain the benefits of hydradermabrasion in a home environment without the need for a clinician, thereby making skin treatment more convenient and more affordable.

Although hydradermabrasion devices suitable for home use are available on the market, there remains room for improvement in the field of home skin treatment devices and more specifically in devices suitable for home use that provide hydradermabrasion.

SUMMARY OF THE INVENTION

The present invention provides a skin treatment device suitable for in-home use that operates in a hydradermabrasion mode to provide skin exfoliation to remove dead skin cells and debris and in a massage mode to provide a facial massage in the presence of red light. The device includes a plurality of interchangeable tips or heads that are used in the hydradermabrasion mode or in the massage mode. For example, in one embodiment, the device is provided with two different hydradermabrasion tips and one massage head. The two different hydradermabrasion tips may be configured differently to treat different regions of the face. In one embodiment, the first tip has a smaller orifice and is intended for use in treating small crevices like the nose area, while the second tip has a larger orifice and is intended for use in treating large areas like the forehead, cheek, and chin. In one embodiment, the massage head does not include an orifice and is not used to provide a jet of fluid or a vacuum, but is instead used to massage the skin after hydradermabrasion with or without topical skin treatments. In one embodiment, the tips and heads are manufactured from silicone rubber or other materials that have similar pliability and resiliency characteristics.

In one embodiment, the device includes a main body, a supply canister, a waste receptacle and a plurality of interchangeable tips or heads. In one embodiment, the main body includes a housing that houses a controller that controls operation of the device largely in response to operator input, a pump that moves liquid through the device when appropriate and a battery that provides electrical power for the system, including the controller and the pump.

In one embodiment, the device includes a head that is configured to removably receive any one of a variety of alternative tips and heads. For example, the main body may include a head that defines a seat upon which a tip or head may be removably mounted. In one embodiment, the seat includes a mounting stem, and each tip and head may be configured to be fitted firmly onto the mounting stem with sufficient frictional engagement to reliably hold the tip or the head on the device until intentionally removed by the user. Additionally or alternatively, the seat defines a recess configured to tightly receive the base of a tip or a head with the desired level of frictional engagement.

In one embodiment, the mounting stem includes a supply port and a return port. The supply port is in fluid communication with the supply canister and provides a portion of the flow path from the supply canister to a tip mounted on the mounting stem. Similarly, the return port is in fluid communication with the waste receptacle and provides a portion of the flow path from a mounted tip to the waste receptacle. The interchangeable tips are configured to be interoperable with the supply port and the return port. More specifically, each tip may define a supply passage that is in fluid communication with the supply port and an return passage that is in fluid communication with the return port.

In one embodiment, each tip includes a suction head that is configured to engage with the surface of the skin to be treated. In one embodiment, the suction head includes a circumferential wall that defines an internal recess. The device includes a supply flow path from the supply canister to the suction head and a waste flow path from the suction head to the waste receptacle. In operation, liquid is moved from the supply canister to the suction head with sufficient force that the liquid jets into the surface of the skin to remove dead skin cells and other debris, and the liquid is drawn away from the suction head into the waste receptacle carrying away the dead skin cells and other debris the waste receptacle.

In one embodiment, the pump draws a partial vacuum in the waste receptacle that draws air/liquid and debris away from the suction head into the waste receptacle. When the suction head is not engaged with the skin, the recess (and consequently the waste flow path) is open to the environment, such that the suction draws air from the environment and no liquid is drawn from the supply canister. However, when the working surface of the suction head is closed by engagement with the user's skin (e.g. face), the suction from the waste receptacle draws liquid from the supply canister to the suction head. Liquid is drawn to suction head with sufficient force for the liquid to jet into the skin to mechanically remove dead skill cells and other debris from the skin.

In one embodiment, the device is capable of operating at a plurality of different suction levels. The different suction levels cause liquid to impinge upon the skin with different levels of force. For example, the suction level of the device can be raised to increase the aggressiveness of the hydradermabrasion or lower to reduce the aggressiveness. In one embodiment, the device includes a controller capable of operating the pump to provide a plurality of different suction levels (or vacuum levels). In one embodiment, the controller is capable of operation at three different suction levels, which may vary from application to application, as desired.

In one embodiment, the supply canister is removable from the main body. The supply canister may be filled with a liquid to be applied to the skin. For example, the supply canister may be filled with water or essentially any topical liquid. In one embodiment, the supply canister is reusable and is refilled by the user as appropriate. If desired, the supply canister can be a single use canister that is recycle or disposed of after use. For example, when it is desirable to perform hydradermabrasion using a topical liquid rather than just water, the topical liquid may be acquired in supply canisters.

In one embodiment, the supply canister is removably fitted to the main body using a friction fit. For example, the mouth of the supply canister may be firmly fitted over a structural seal extending from the main body. More specifically, the mouth of the canister may configured to tightly interface with the supply canister mounting seal. The supply canister may be configured to closely interface with another portion of the device when installed. For example, the supply canister may interface with the waste receptacle when properly installed. The interface may be as simple as adjacent positioning of the supply canister and the waste receptacle or it may be more complex with at least a portion of the supply canister shaped to interfit with at least a portion of the waste receptacle.

In one embodiment, the device includes a battery-operated pump that provides a partial vacuum used to move the fluid from the supply canister, through the tip and then into the waste receptacle. In one embodiment, the battery is a rechargeable Li-ion battery with, for example, a capacity of 650 mA.

In one embodiment, the controller includes a sensor configured to determine the orientation of the device and to prevent operation of the pump when the device is not at an appropriate angle for operation. For example, in the illustrated embodiment, the pump creates a partial vacuum within the waste receptacle by withdrawing air from the head space in the waste receptacle. If the device is inverted during operation, the pump inlet will be submerged in waste liquid, which will cause the pump to withdraw waste liquid from the waste receptacle rather than air. This would prevent proper operation of the device and could lead to unwanted discharge of waste liquid from the device.

In one embodiment, the controller includes a liquid level sensor configured to determine the water level in the waste receptacle. For example, in one embodiment, the controller includes a sensor disposed at the top of the waste receptacle to determine the liquid level in the waste receptacle and to prevent operation of the pump when the waste receptacle is full. This helps to prevent the pump from withdrawing waste liquid from the waste receptacle, which would prevent proper operation of the device and could lead to unwanted discharge of waste liquid from the device.

In one embodiment, the device includes a red LED that can be illuminated as desired, for example, during massage mode to provide red LED therapy.

The current embodiments provides an in-home device that is effective and reliable, and that can be used for both hydradermabrasion and massage therapy. The device can be provided with a plurality of interchangeable tips that facilitate more effective use in different regions of skin and for different applications. Further, the device can be provided with one or more interchangeable heads that can be used for massage therapy. The integrated waste receptacle provides storage for waste that is easily emptied while remaining affixed to the main body so that it is not easily lost. The waste receptacle can be closed by a pliable and resilient plug that is easily removed from the bottom of the waste receptacle to facilitate closing. The plug may also be fitted to the bottom of the supply canister and include a living hinge so that when the plug is removed form the waste receptacle it remains attached to the device by virtue of its connection to the supply canister. This helps to avoid loose parts that may become lost. The device may include an angle sensor that prevents operation of the pump when the device is at an angle that may result in improper operation. The device may also include a liquid level sensor to prevent operation of the pump when the supply canister is empty.

These and other objects, advantages, and features of the invention will be more fully understood and appreciated by reference to the description of the current embodiment and the drawings.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

DETAILED DESCRIPTION OF THE CURRENT EMBODIMENTS

Figure 1:
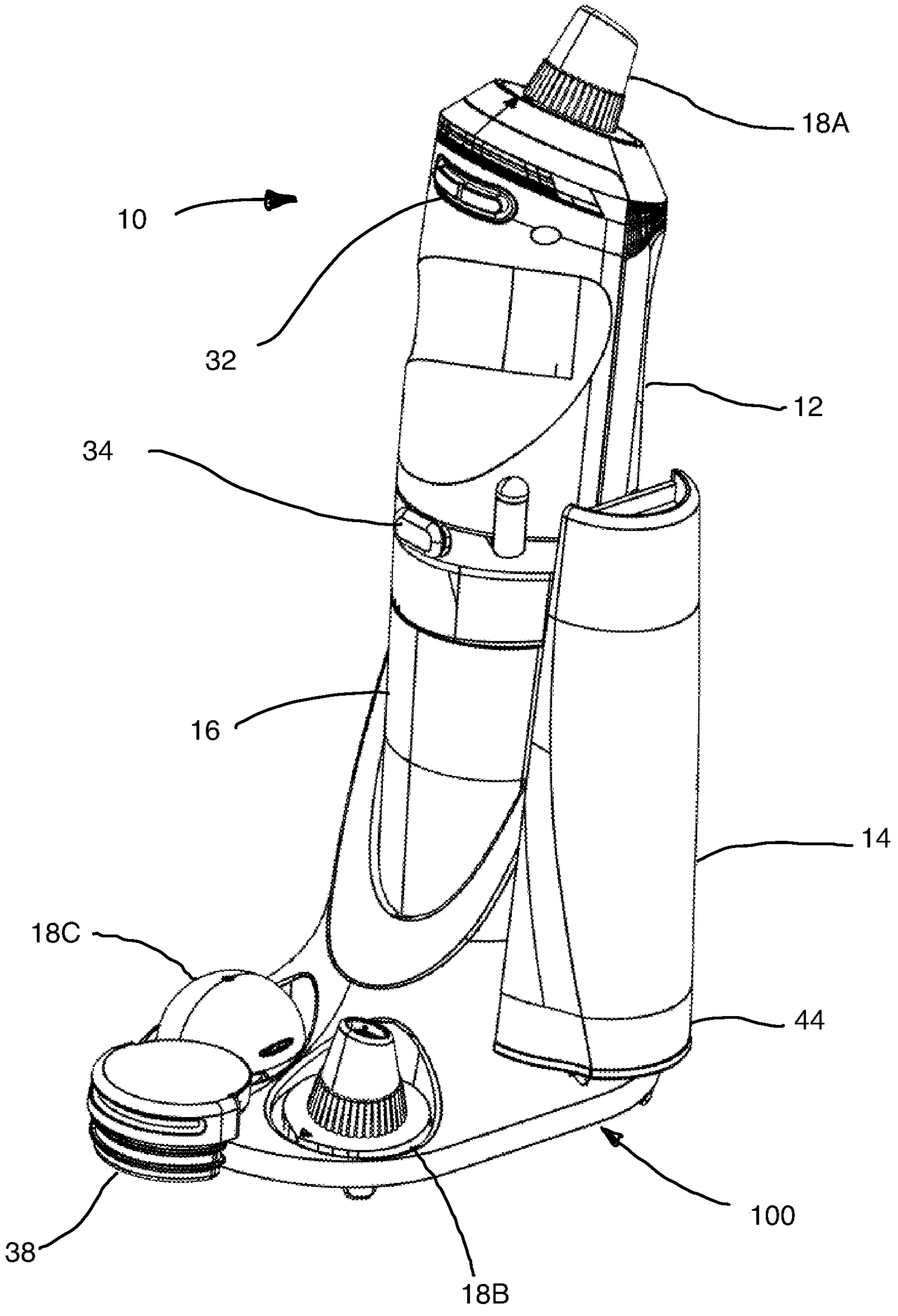
FIG. 1 is a perspective view of a skin resurfacing device and various accessories in a cradle.
Figure 2:
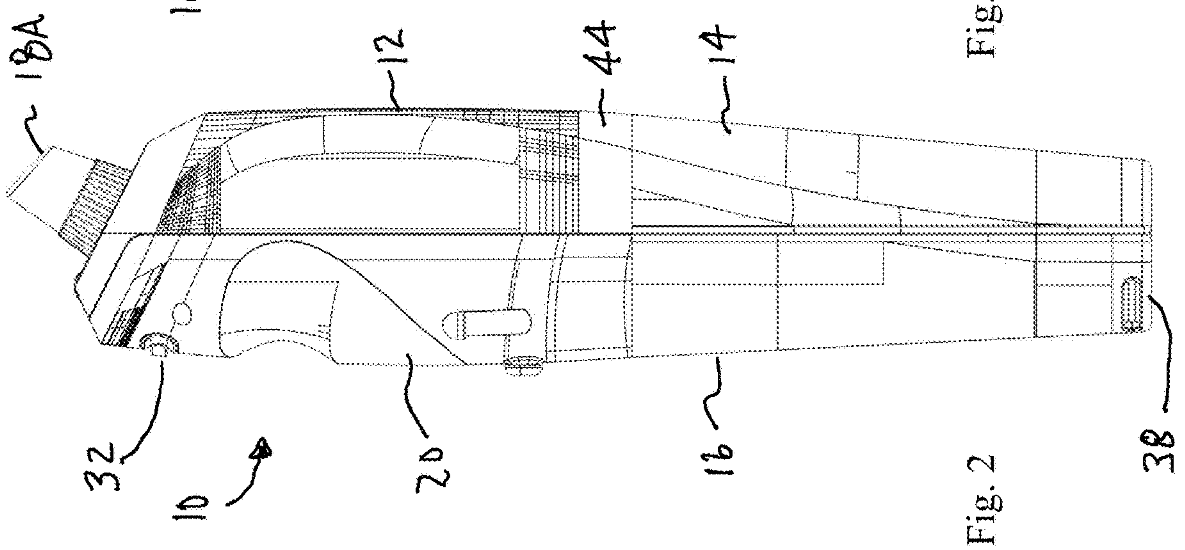
FIG. 2 is a side view of the device with a first tip installed.
Figure 3:
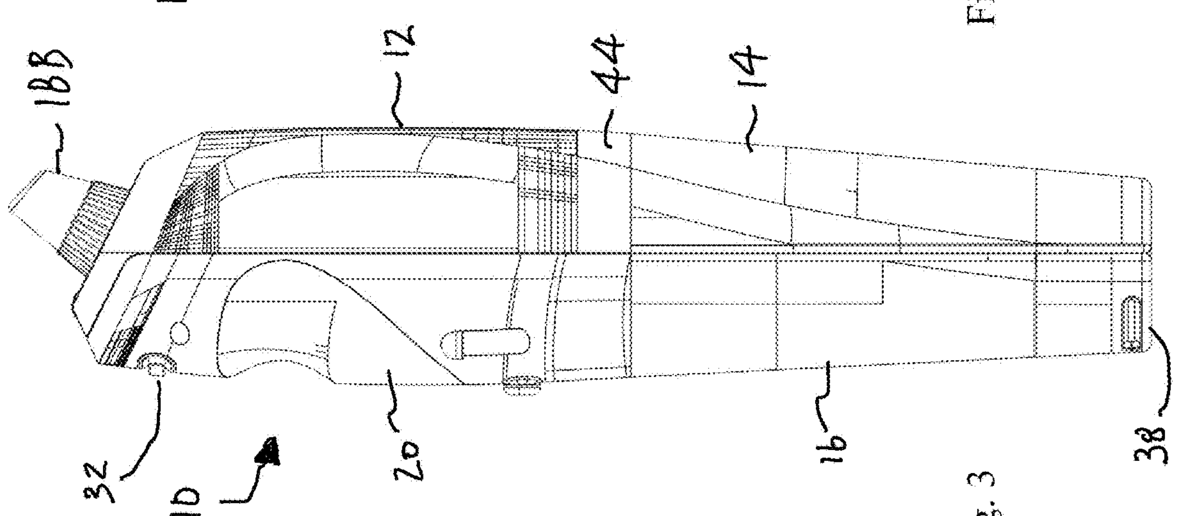
FIG. 3 is a side view of the device with a second tip installed.
Figure 4:
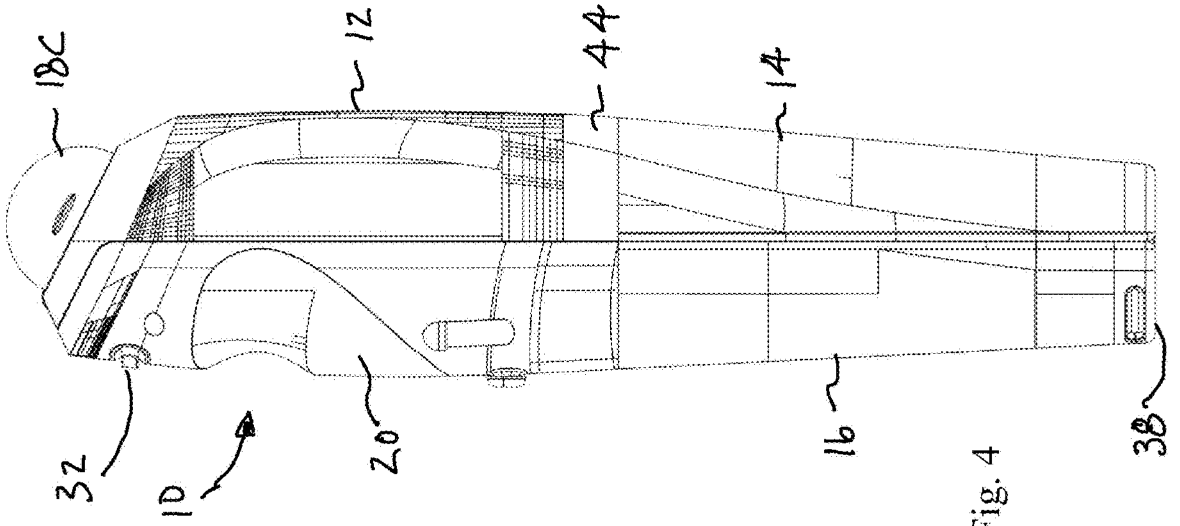
FIG. 4 is a side view of the device with a massage head installed.

A current embodiment of the skin treatment device is shown in FIGS. 1-4 and generally designated 10. The skin treatment device 10 is suitable for in-home use and operates in hydradermabrasion mode to provide skin exfoliation to remove dead skin cells and debris and in massage mode to provide a facial massage, optionally while providing red light therapy. In the illustrated embodiment, the device 10 generally includes a main body 12, a supply canister 14, a waste receptacle 16 and a plurality of replaceable tips or heads 18A, 18B and 18C. The supply canister 14 of this embodiment is removable from main body 12 for replacement and/or filling. The waste receptacle 16 is configured to remain in place on the main body 12, and includes a removable plug 38 in the bottom end that can be easily removed by the user to empty the waste receptacle 16. FIG. 1 shows the skin treatment device 10 stored in a storage cradle 100 with the supply canister 14 and plug 38 removed and seated on the cradle 100, and with the first tip 18A installed on the device 10 and the second tip 18B and massage head 18C seated on the cradle 100. FIG. 2 shows the skin treatment device 10 with tip 18A installed. FIG. 3 shows the device 10 with tip 18B installed. FIG. 4 shows the device 10 with massage head 18C installed.

The present invention will now be described in more detail with reference to the embodiment shown in the drawings. As noted above, the skin resurfacing device 10 generally includes a main body 12, a supply canister 14, a waste receptacle 16 and a plurality of replaceable tips or heads 18A, 18B and 18C. The supply canister 14 of the illustrated embodiment is removable from the main body 12. The supply canister 14 may be filled with a liquid to be applied to the skin by the device 10. For example, the supply canister 14 may be filled with water or essentially any topical liquid. In the illustrated embodiment, the supply canister 14 is configured to be reusable and is repeatedly refilled by the user as appropriate. In alternative applications, the supply canister 14 can be a single use canister that is used once and then recycled or disposed of after use. For example, when it is desirable to perform hydradermabrasion using a commercially obtained topical liquid (rather than just water), the topical liquid may be acquired from a supplier in alternative single-use supply canisters.

Figure 9:
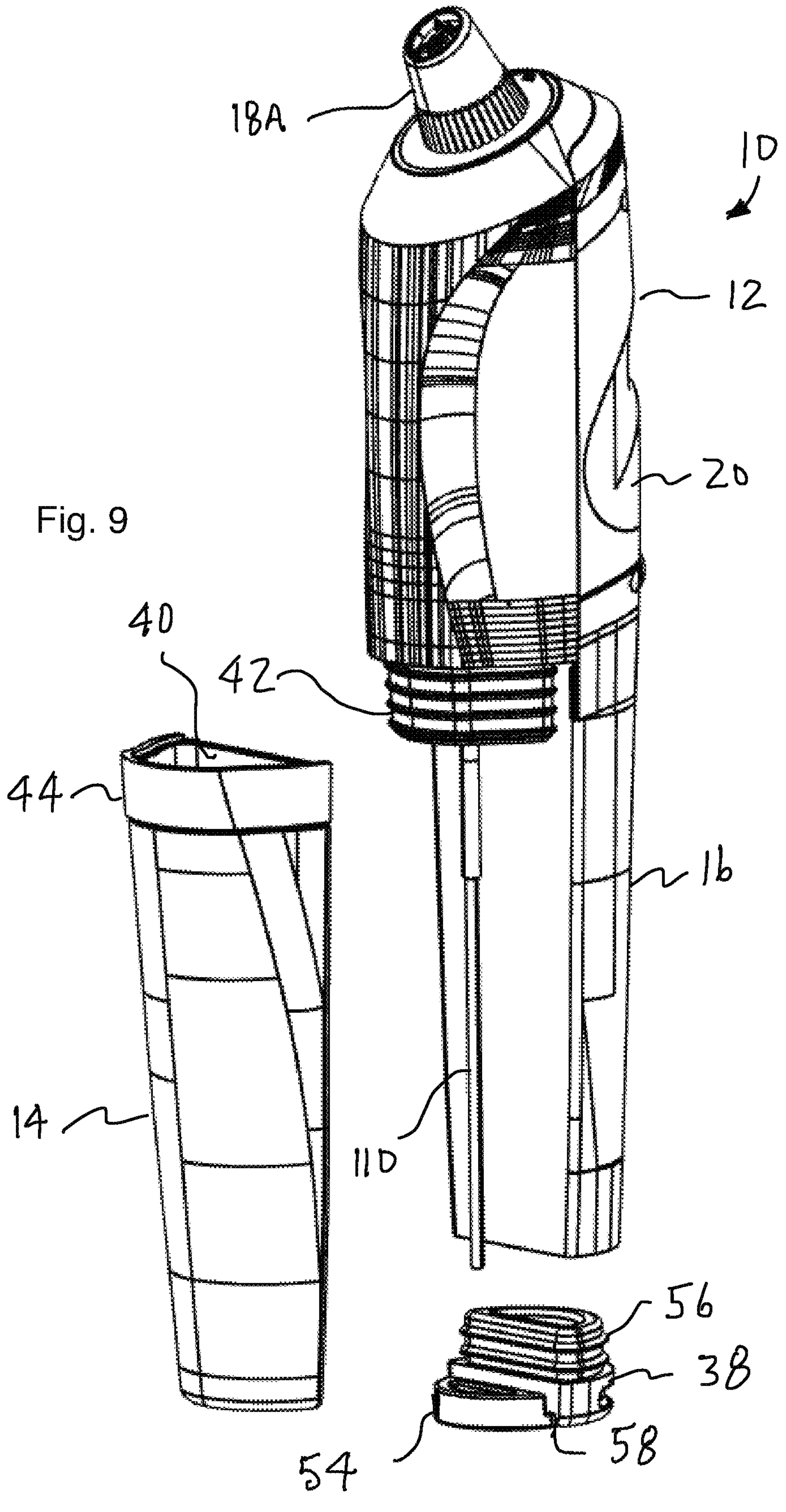
FIG. 9 is a partially exploded perspective view of the device with the supply canister and the plug removed.

In the illustrated embodiment, the supply canister 14 is removably fitted to the main body 12 through the use of a friction fit. For example, the mouth 40 of the supply canister 14 may be configured to firmly seat over a structural seal extending from the main body 12. More specifically, the mouth 40 of the canister may be configured to tightly interface with a supply canister mounting seal 42. The supply canister mounting seal 42 is manufactured from a pliable, resilient material, such as silicone rubber or other materials suitable for forming a structural and leak-tight seal between the supply canister 14 and the main body 12. The supply canister 14 may be configured to closely interface with one or more other portions of the device 12 when installed. For example, the supply canister 14 may interface with the waste receptacle 16 when properly installed on the main body 12. The interface may be as simple as adjacent positioning of the supply canister 14 and the waste receptacle 16 or it may be more complex with the supply canister 14 and/or waste receptacle 16 shaped to mechanically interfit with one another. As shown in FIG. 9, the supply canister 14 of the illustrated embodiment includes a trim 44 that is fitted to the exterior of the supply canister 14 about the mouth 40. In this embodiment, the trim 44 is generally U-shaped covering the uppermost end of the exposed outer surface of the supply canister 14. In alternative applications, the trim 44 may be eliminated or may have a different design and/or configuration. In the illustrated embodiment, the bottom end of the supply canister 14 includes a recess 52 configured to receive a portion of the plug 38 (as described in more detail below).

The waste receptacle 16 of the illustrated embodiment is secured to the main body 12 and is configured to remain in place on the main body 12 permanently. The waste receptacle 16 includes an open upper end 46 that is fitted to a structural seal that retains the waste receptacle 16 and prevents leaks. More specifically, the open end 46 of the waste receptacle 16 may be configured to tightly interface with a waste receptacle 16 mounting seal 50. The waste receptacle mounting seal 50 is manufactured from a pliable, resilient material such as silicone rubber or other materials suitable for forming a structural and leak-tight seal between the waste receptacle 16 and the main body 12. The waste receptacle 16 includes an open bottom end 48 that is selectively closed by the plug 38. As shown, the plug 38 is configured to be fitted tightly into the bottom end 48 end to close the waste receptacle 16 so that it retains waste liquid accumulating in the waste receptacle 16. The plug 38 is manufactured from a pliable, resilient material such as silicone rubber or other materials suitable for forming a leak-tight closure for the waste receptacle 16. In the illustrated embodiment, the plug 38 includes a retention portion 54, a closure portion 56 and a hinge portion 58. The retention portion 54 is configured to attach to the bottom end of the supply canister 14. For example, as noted above, the supply canister 14 may include a recess 52 configured to firmly receive the retention portion 54 of the plug 38. The closure portion 56 includes a neck 60 that is fitted into the open bottom end 48 of the waste receptacle 16 and a head 62 that prevents the closure portion 56 from being pushed too far into the bottom end 48. The hinge portion 58 joins the retention portion 54 and the closure portion 56. The hinge portion 58 allows the plug 38 to remains affixed to the device 10 even when the closure portion 56 is removed from the waste receptacle 16 for emptying. In the illustrated embodiment, the plug 38 is a one-piece molded component in which the hinge portion 58 is a living hinge that is formed integrally with the retention portion 54 and the closure portion 56. As shown in FIG. 1, the plug 38 can be entirely removed from the device 10 and stored in a corresponding plug seat 64 on the cradle 100. The cradle 100 of the illustrated embodiment includes a seat 150 capable of receiving and supporting the device 10 with the supply canister 14 removed, a supply canister recess 152 in which a portion of the supply canister 14 can be fitted to hold the supply canister 14 in an inverted position, a first tip seat 154 capable of receiving a first working attachment and a second tip seat 156 capable of receiving a second working attachment. The design and configuration of the cradle 100 may vary from application to application, as desired.

As noted above, the skin resurfacing device 10 includes a plurality of interchangeable working attachments that are selectively attached to the device 10 and are configured for selective use in either hydradermabrasion mode or in massage mode. For example, in the illustrated embodiment, the device 10 is provided with two different hydradermabrasion tips 18A and 18B and one massage head 18C. In alternative applications, the number, design and configurations of interchangeable working attachments (e.g. tips and heads) may vary from application to application as desired. In the illustrated embodiment, the various working attachments 18A, 18B and 18C have similar shape with respect to the portions that interface with the device 10 so that the working attachments 18A, 18B and 18C can be interchangeably installed on the working end of the device 10. As discussed in more detail below, each illustrated working attachment 18A, 18B, 18C includes a base 70A, 70B and 70C that is configured to be seated in the working end of the device 10 and a stem receptacle (not shown) that is configured to be fitted over the mounting stem 68 when the base is proper seated. In the illustrated embodiment, the stem receptacle is a void of approximately the same size and shape as the mounting stem 68. The size, shape and configuration of the mounting stem 68 and the stem receptacle may be varied from application to application, as desired. For example, the stem receptacle may be reduced slightly to tighten the fit and provide an enhanced leak-tight seal. As another example, the mounting stem 68 and the stem receptacle may include mating features (e.g. rib and channel) that interfit when the working attachment is fully seated to provide a snap-together function. To provide supply and return flow paths, hydradermabrasion tips 18A and 18B define a supply through hole 78 and a return through hole 80. In the illustrated embodiment, the mounting stem 68 includes a supply passage 116 through which liquid flows to the working attachment and a return passage 118 through which liquid and debris flow to the waste receptacle 16. The supply passage 116 terminates at a supply port 112 that is, in turn, in fluid communication with the supply through hole 78 passing through the tip 18A and 18B. Similarly, the return passage 118 terminates as a return port 114 that is in fluid communication with the return through hole 80 passing through the tip 18A and 18B.

Figure 5:
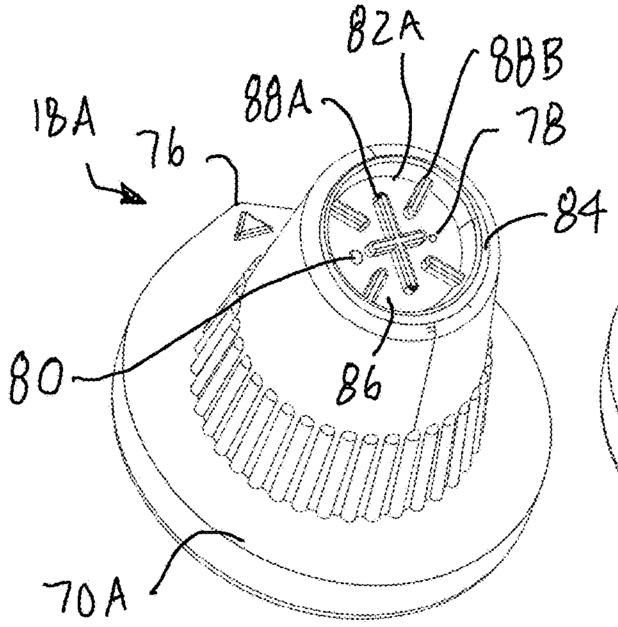
FIG. 5 is a perspective view of the first tip.
Figure 6:
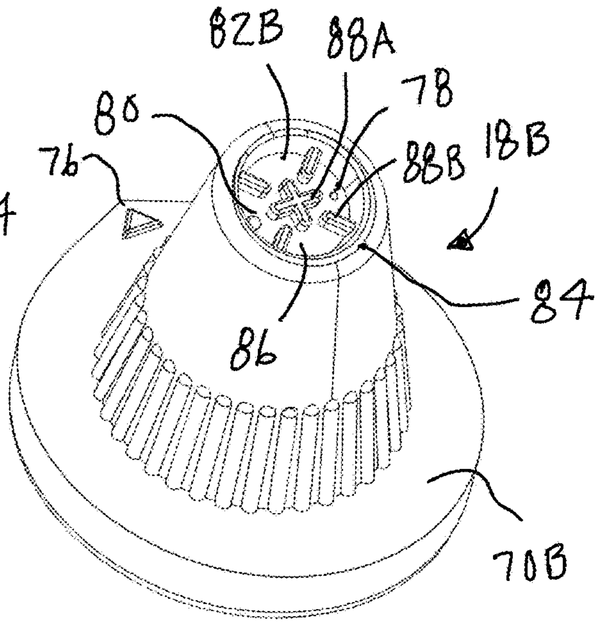
FIG. 6 is a perspective view of the second tip.
Figure 7:
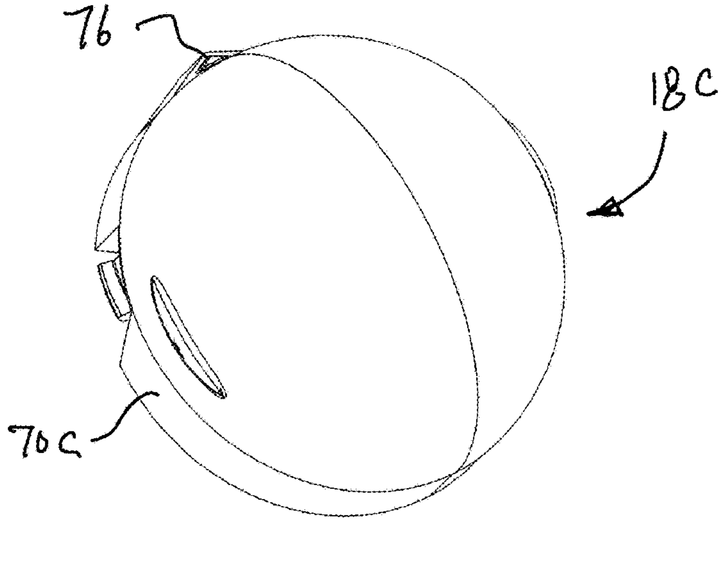
FIG. 7 is a perspective view of the massage head.

The three different working attachments 18A, 18B and 18C are shown installed on the device 10 in FIGS. 2-4 and separate from the device 10 in FIGS. 5-7. Tips 18A and 18B are designed for use in hydradermabrasion mode. These two tips 18A and 18B each have an outer surface 82A and 82B that is configured to provide a suction head that can be moved over the skin during hydradermabrasion. In the illustrated embodiment, the outer surface 82A and 82B is generally circular, but its shape may vary from application to application. Each outer surface 82A and 82B has a peripheral protrusion 84 that protrudes to define an internal region 86. In the illustrated embodiment, the peripheral protrusion 84 is generally circular circumferential wall that is disposed about the periphery of the outer surface 82A and 82B, but its size, shape and location may vary from application to application. The supply through hole 78 and the return through hole 80 open into the internal region 86 to allow liquid and vacuum to be supplied to the internal region 86 via the supply through hole 78 and the return through hole 80. The size, shape and configuration of the through holes 78 and 80 may vary from application to application to control or tune the manner in which liquid is introduced to the skin and drawn away from the tip 18A and 18B. For example, it may be desirable to tune the size of the supply through hole 78 and the return through hole 80 so that liquid entering the internal region 86 jets into the skin with the desired characteristics (e.g. volume and velocity). In the illustrated embodiment each tip 18A and 18B also includes one or more inner protrusions on the outer surface 84 within the inner region 86. For example, the illustrated tips 18A and 18B each include a generally "+"-shaped inner protrusion 88A at the approximate center of the inner region 86 and a plurality of radial protrusions 88B that extend radially inward from the peripheral protrusion 84. In this embodiment, the inner protrusions 88A, 88B are rounded and smooth, and are shorter than the peripheral protrusion 84, but their size, shape and relative height may vary from application to application. Although both tips 18A and 18B are generally frustoconical, the two tips 18A and 18B are configured differently to allow them to more effectively treat different regions of the face. The first tip 18A of the illustrated embodiment has a somewhat shorter and wider frustoconical shape with a smaller supply through hole 78. First tip 18A is intended for use in treating large areas like the forehead, cheek, and chin. The second tip 18B is somewhat taller and tapers to a smaller diameter. This tip 18B has a larger supply through hole 78 and is intended for use in treating smaller crevices like the nose area. Although the illustrated embodiment includes two alternative hydradermabrasion tips, the number of interchangeable tips provided with the device 10 or obtainable separately from the device 10 may vary.

Head 18C is configured for use in applying massage to the skin, for example, after hydradermabrasion or independent of hydradermabrasion. In the illustrated embodiment, the massage head 18C is domed (e.g. generally semi-spherical) with a smooth outer surface, which facilitates use in applying a massage the skin, with or without topical skin treatments. The massage head 18C of the illustrated embodiment does not include any supply or return orifices as the device 10 does not distribute liquid when in massage mode. The size, shape and configuration of the massage head 18C may vary from application to application. In some applications, the device 10 may be provided with a plurality of different massage heads that are specially configured for different applications.

Figure 8:
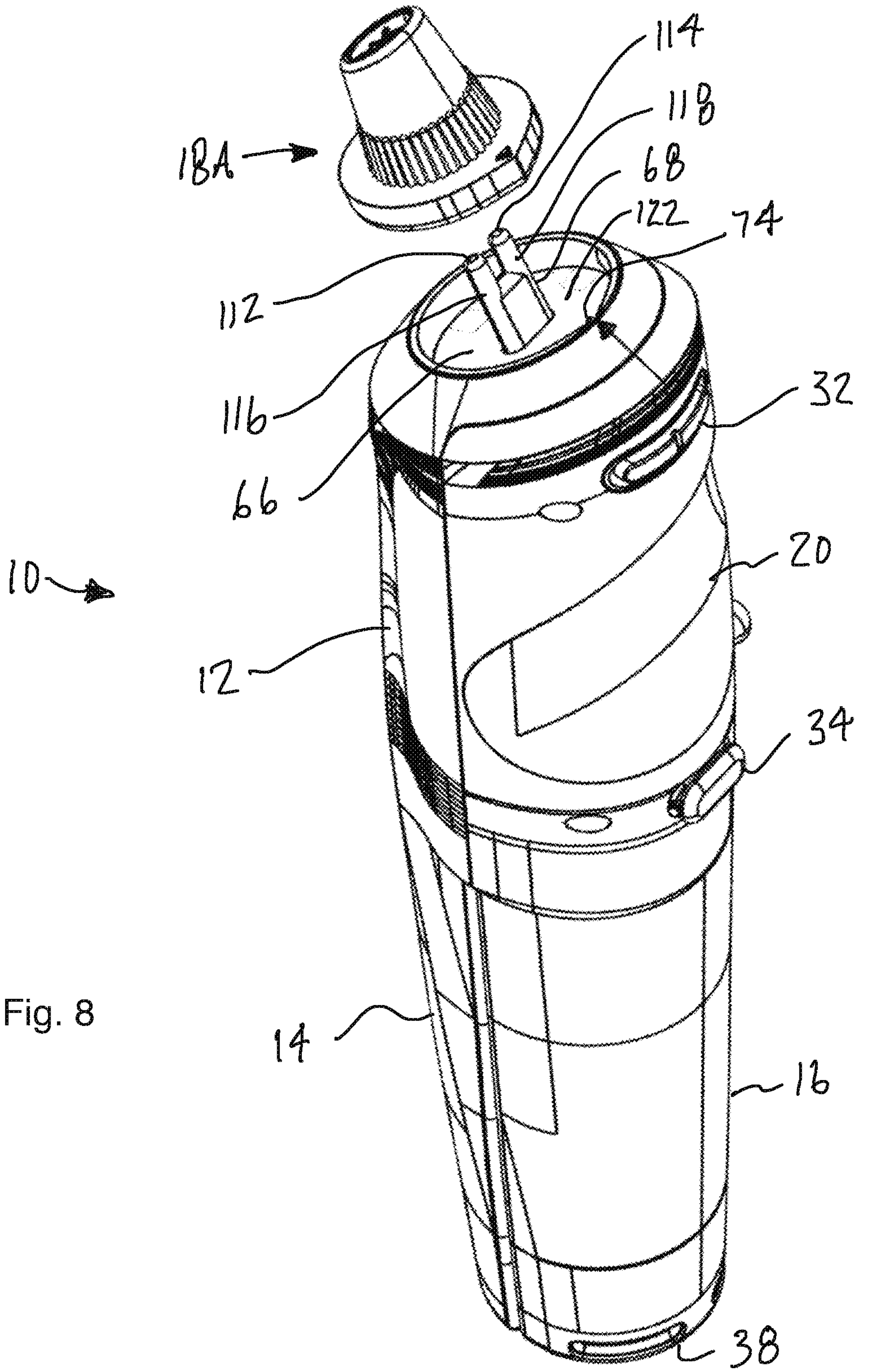
FIG. 8 is a partially exploded perspective view of the device with the first tip removed.
Figure 14:
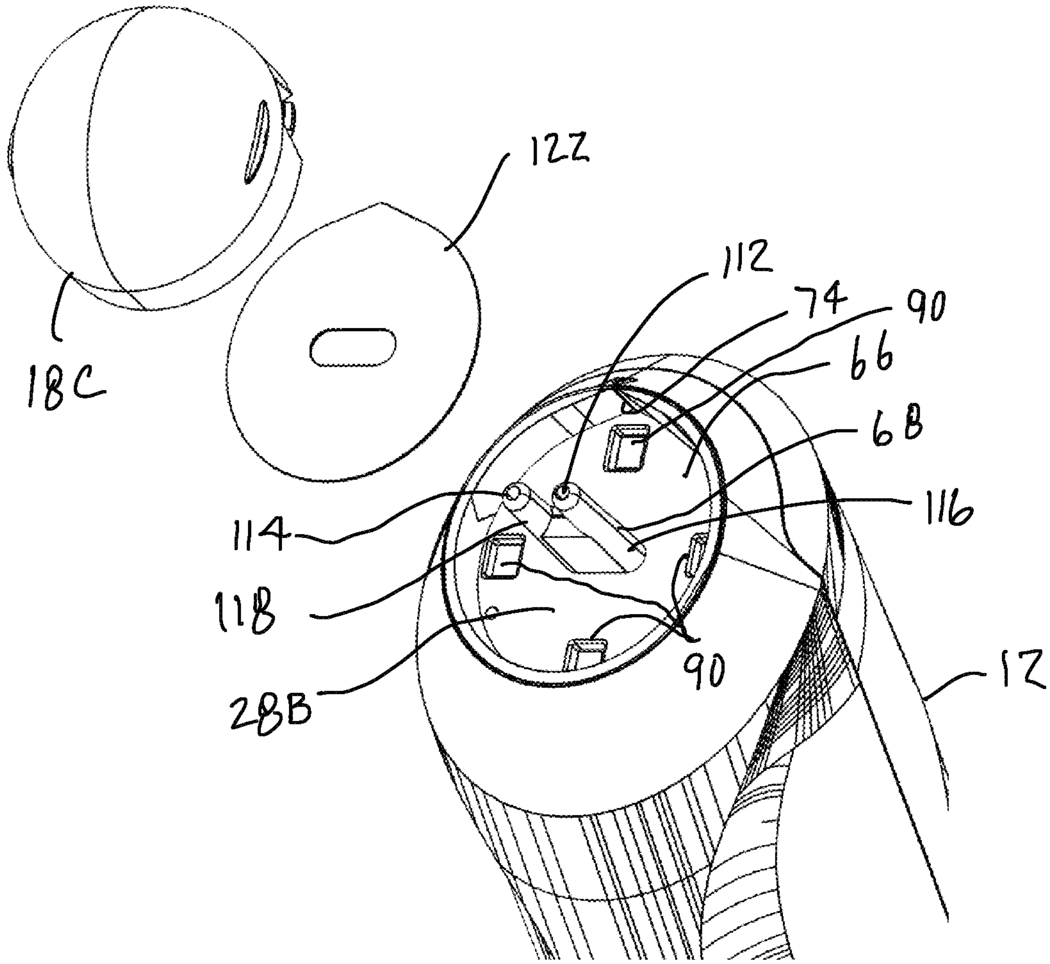
FIG. 14 is a partially exploded perspective view of a portion of the device with the massage head and diffuser sheet removed.
Figure 15:
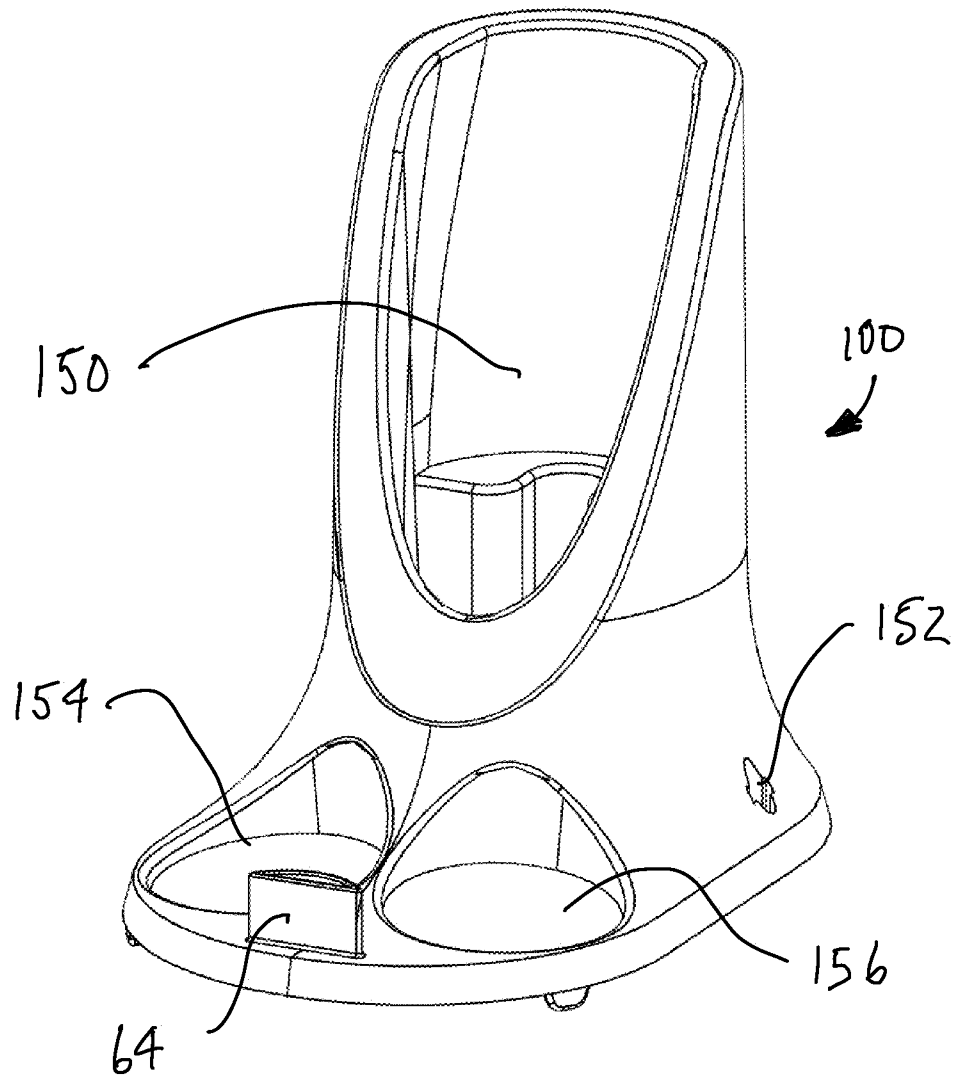
FIG. 15 is a perspective view of the cradle with the device and all accessories removed.
Figure 16:
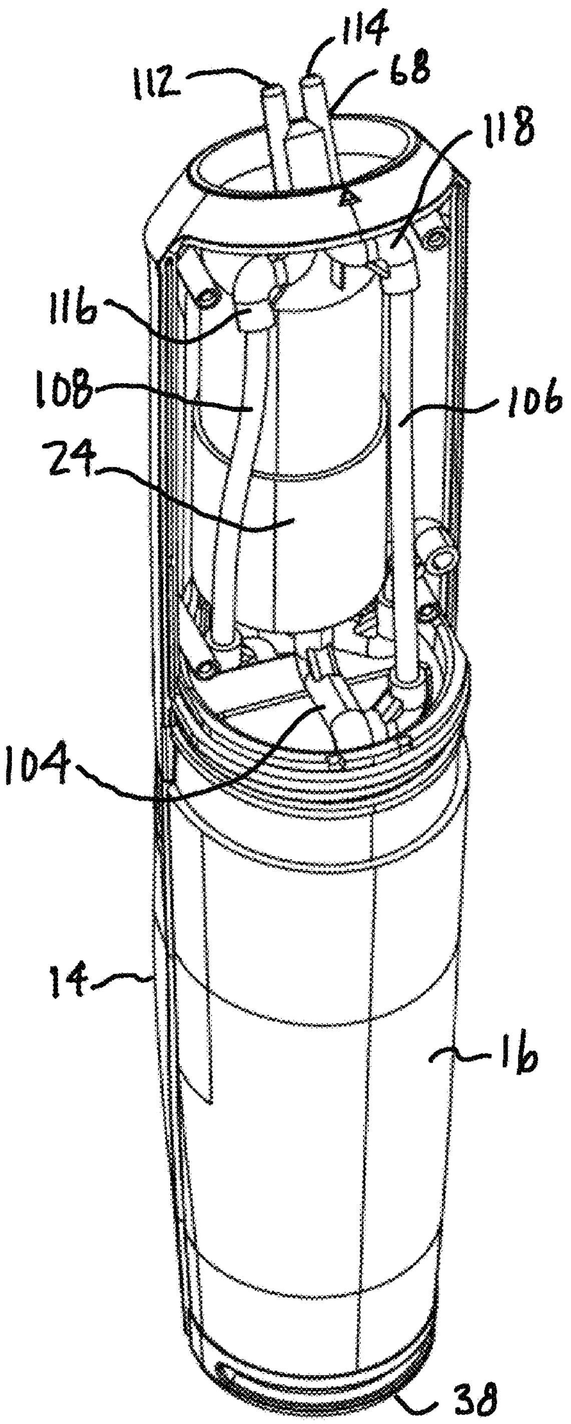
FIG. 16 is a first perspective view of the device with portions removed to show the liquid and air flow paths.
Figure 17:
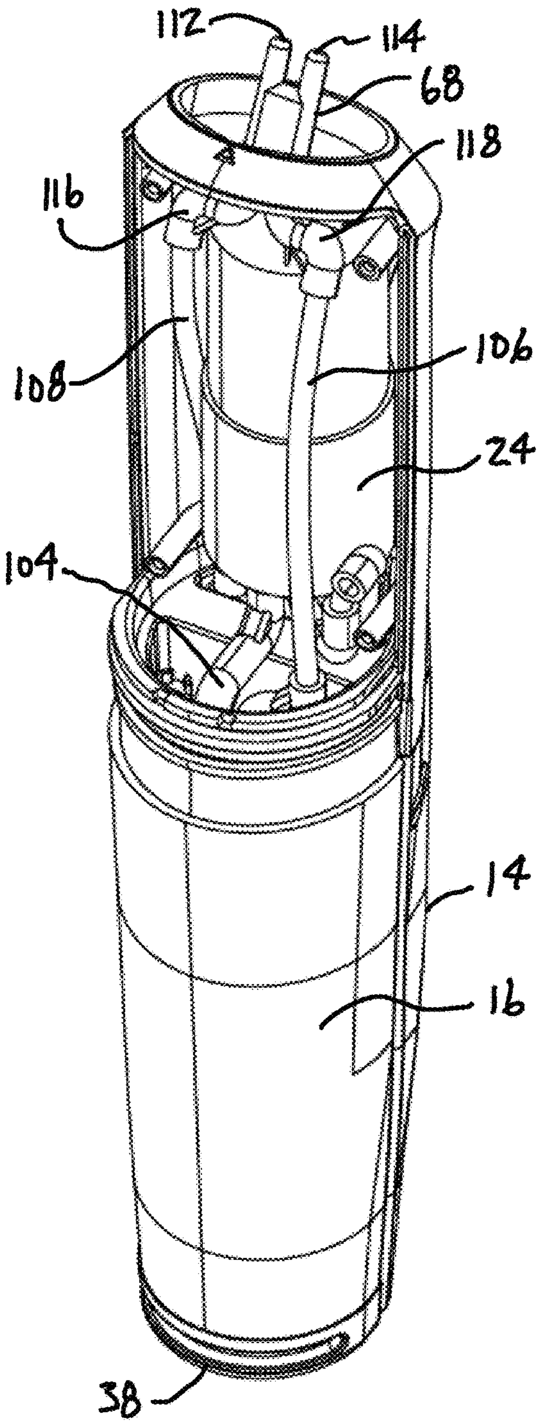
FIG. 17 is a second perspective view of the device with portions removed to show the liquid and air flow paths.

As discussed briefly above, the three interchangeable working attachments of the illustrated embodiment (i.e., tips 18A, 18B and head 18C) are configured to mount to a common mounting structure provided at the top end of the device 10. As shown in FIGS. 8 and 14, the top end or working end of the device 10 defines a recess 66 and a mounting stem 68. The recess 66 is shaped to receive the base 70A, 70B or 70C of the tips 18A or 18B or the base of the massage head 18C. To facilitate proper rotational alignment, the recess 66 and the bases of the tips/head may be keyed so that they fit together only in the proper rotational orientation. For example, as shown, the recess 66 may have an asymmetric feature 74 that receives a corresponding asymmetric feature 76 on each base 70A, 70B and 70C so that each base 70A, 70B or 70C can be properly installed in the mounting recess 66 in a single rotational orientation in which the asymmetric features 74 and 76 are aligned. In the illustrated embodiment, the mounting stem 68 is configured to be fitted into a corresponding stem receptacle 72A, 72B and 72C in each working attachment 18A, 18B and 18C.

In the illustrated embodiment, the tips and head are manufactured from silicone rubber or other materials that have similar pliability and resiliency characteristics. The pliable, resilient nature allows each working attachment 18A, 18B and 18C to be easily frictionally fitted to and removed from the device 10. More specifically, the base 70A, 70B and 70C can be tightly received in this recess 66 and the stem receptacle 72A, 72B and 72C can be tightly fitted over the mounting stem 68. In alternative embodiments, the working attachments can be interchangeably affixed to the working end of the device 10 using essentially any attachment method capable of retaining the working attachments during use. In the illustrated embodiment, the device 10 is configured to provide red light therapy (as discussed in more detail below). In this embodiment, red light is generated by light sources disposed below the tips and heads. To allow the transmission of red light from the device 10 to the skin, the massage head 18C is transparent or translucent. In applications where it may be desirable to provide red light therapy during hydradermabrasion mode, the tips 18A and 18B may also be transparent or translucent.

The main body 12 generally includes a housing 20, a control system 22, a pump 24, a battery 26 and a plurality of flow passages (as described in more detail below) that provide for the flow of air and liquid through the device 10. The housing 20 encloses the control system 22, the pump 24, the battery 26 and the flow passages. The control system 22 may include a collection of electronic components that are supported on one or more PCB assemblies. For example, in the illustrated embodiment the control system 22 includes a main PCB 28A and a head PCB 28B. The main PCB 28A supports a controller 30 and other suitable electronic components as described herein and as would otherwise be known to those skilled in the field. The head PCB 28B supports an array of red LEDs 90 that are configured to selectively provide red light therapy. In alternative embodiments, the electronics may be distributed over one or more separate PCBs as desired. The controller 30 may be essentially any type of electronic controller, such as a microcontroller or microcontroller unit ("MCU"), that includes suitable programming to operate the device 10 in accordance with the description set forth herein. In alternative applications, control of the device may be distributed over more than one controller. The control system 22 may also include one or more switches 92A and 92B mounted to the main PCB 28A that function as inputs and are part of the user interface as described in more detail below. The control system 22 may also include an array of LEDs 96, 98, 100 and 102A-B that are mounted to the PCB 28A near the switches 92A and 92B, and that are also part of the user interface as described in more detail below.

In the illustrated embodiment, the pump 24 is selectively operated to move from the supply canister 14 liquid through the device 10. More specifically, in the illustrated embodiment, the pump 24 draws a partial vacuum in the waste receptacle 16 that is capable of drawing liquid from the supply canister 14 to a working attachment (e.g. tip 18A and 18B) and from the working attachment into the waste receptacle 16 as described in more detail below. The pump 24 may be essentially any pump capable of fitting into the form factor of the device 10 and of providing the desired flow rates. In the illustrated embodiment, the device 10 includes a battery-operated pump 24, but other types of pumps may be used in alternative embodiments. In the illustrated embodiment, the battery 26 provides power to the control system 22 and all electronic components. The illustrated battery 26 is a rechargeable Li-ion battery with a capacity of 650 mA. The number, type of battery and/or other electrical storage device and its capacity may vary from application to application.

In the illustrated embodiment, the device 10 includes a plurality of flow passages that direct the flow of air and liquid through the device 10. These flow passages allow the pump 24 to draw a partial vacuum in the waste receptacle 16 and to use that partial vacuum to jet liquid into the skin and to move waste liquid and other debris from the skin to the waste receptacle. The illustrated pump 24 is in fluid communication with the waste receptacle 16 via a vacuum line 104 so that when the pump 24 is operating, it draws fluid, typically air, from can draw a partial vacuum in the waste receptacle 16. A return line 106 is connected between the waste receptacle 16 and the return port 114 of the mounting stem 68. This allows the partial vacuum in the waste receptacle 16 to be communicated to a working attachment (e.g. tip 18A or 18B) seated on the mounting stem 68. The partial vacuum allows liquid and debris to be drawn from away from the skin into the waste receptacle 16. A supply line 108 is connected between the supply canister 14 and the supply port 112 of the mounting stem 68. The supply line 108 provides a flow passage which allows a partial vacuum developed at the working attachment to draw liquid from the supply canister 14 to the working attachment. In the illustrated embodiment, the supply line 108 is in communication with a supply tube 110 that disposed within the supply canister 14 and extends to a point at or near the bottom of the supply canister 14. In the illustrated embodiment, the liquid is drawn from the supply canister 14 to the working attachment with sufficient force for the liquid to jet into the skin as appropriate to provide hydradermabrasion. The characteristics of the jet of liquid engaging the skin may be varied from time to time or from application to application by adjusting the flow rate of liquid through the device 10 and/or the characteristics of the flow path. For example, the characteristics of the working attachment, such as the supply through hole 80, the characteristics of the mounting stem 68, such as the supply port 112, may be varied to tune the properties of the liquid engaging the skin. As another example, the device 10 may be configured to selectively operate the pump 24 at different flow rates to selectively vary the volume of liquid moving through the device 10 and the force at which the liquid jets into the skin. The flow rate of the pump 24 may be set by the controller and/or by the user. In the illustrated embodiment, the pump 24 is capable of operating at a plurality of different flow rates. The different flow rates provide different suction levels that cause liquid to impinge upon the skin with different levels of force. For example, the flow rate of the pump 24 can be raised to increase the aggressiveness of the hydradermabrasion or lowered to reduce the aggressiveness. The device 10 of the illustrated embodiment includes a controller 30 capable of operating the pump 24 at three different flow rates (or vacuum levels). In the illustrated embodiment, the user may select the desired flow rate (or vacuum level). In some applications, the flow rate may be set automatically based on the mode of operation set by the user. The specific flow rates and the number of alternative flow rates may vary from application to application, as desired.

In the illustrated embodiment, the control system 22 includes a sensor 120 configured to determine the orientation of the device 10, such as a BL-108 angle sensor. The output of the sensor 120 is used by the controller 30 to prevent operation of the pump 24 when the device 10 is not at an appropriate angle for operation. For example, in the illustrated embodiment, the pump 24 creates a partial vacuum within the waste receptacle 16 by withdrawing air from the head space at the top of the waste receptacle 16. If the device 10 is inverted during operation, the inlet from the pump 24 may be submerged in waste liquid, which could cause the pump 24 to withdraw waste liquid from the waste receptacle 16 rather than air. This could interfere with proper operation of the device 10 and lead to unwanted discharge of waste liquid from the pump 24.

In the illustrated embodiment, the device 10 is configured to automatically shut off the pump 24 when the waste receptacle 16 is full, thereby preventing overfilling. The control system 22 of the illustrated embodiment includes a liquid level sensor 122 configured to provide a signal to the controller 30 when the waste receptacle 16 is full. For example, in the illustrated embodiment, a liquid level sensor 124 is mounted to the main PCB 28A and includes two sensor pins 124A and 124B that extend into the top of the waste receptacle 16. When the liquid level reaches the sensor pins 124A and 124B, an electrical flow path is provided between the two sensor pins 124A and 124B and the level sensor 124 generates a corresponding signal. Upon receiving the signal, the controller 30 can prevent operation of the pump 24 until the waste receptacle 16 is emptied. The controller 30 may also provide user feedback, such as illumination of an LED or production of an audible signal, to advise the user that the waste receptacle 16 is full and needs to be emptied.

Figure 10:
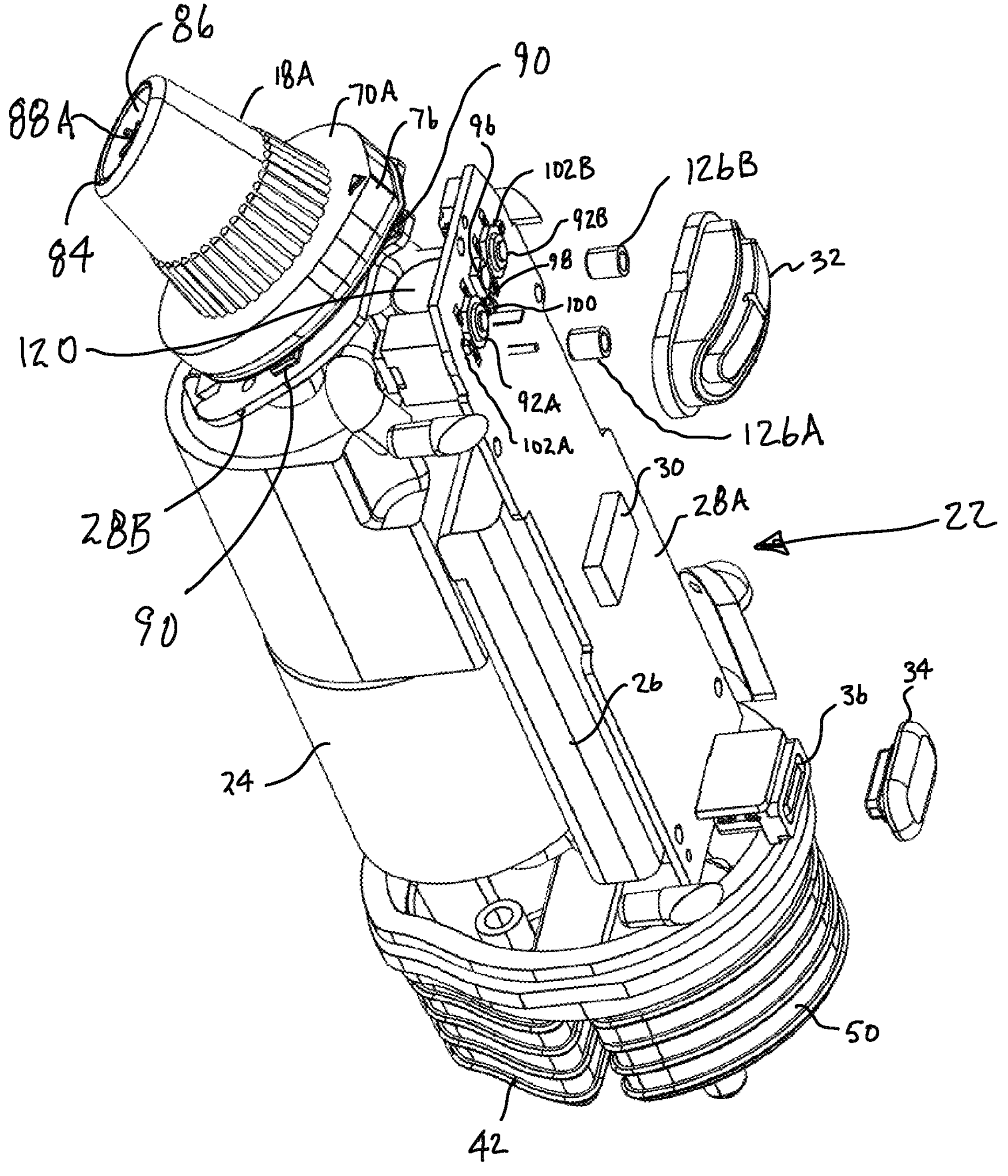
FIG. 10 is a first partially exploded perspective view of the main body with portions removed.
Figure 11:
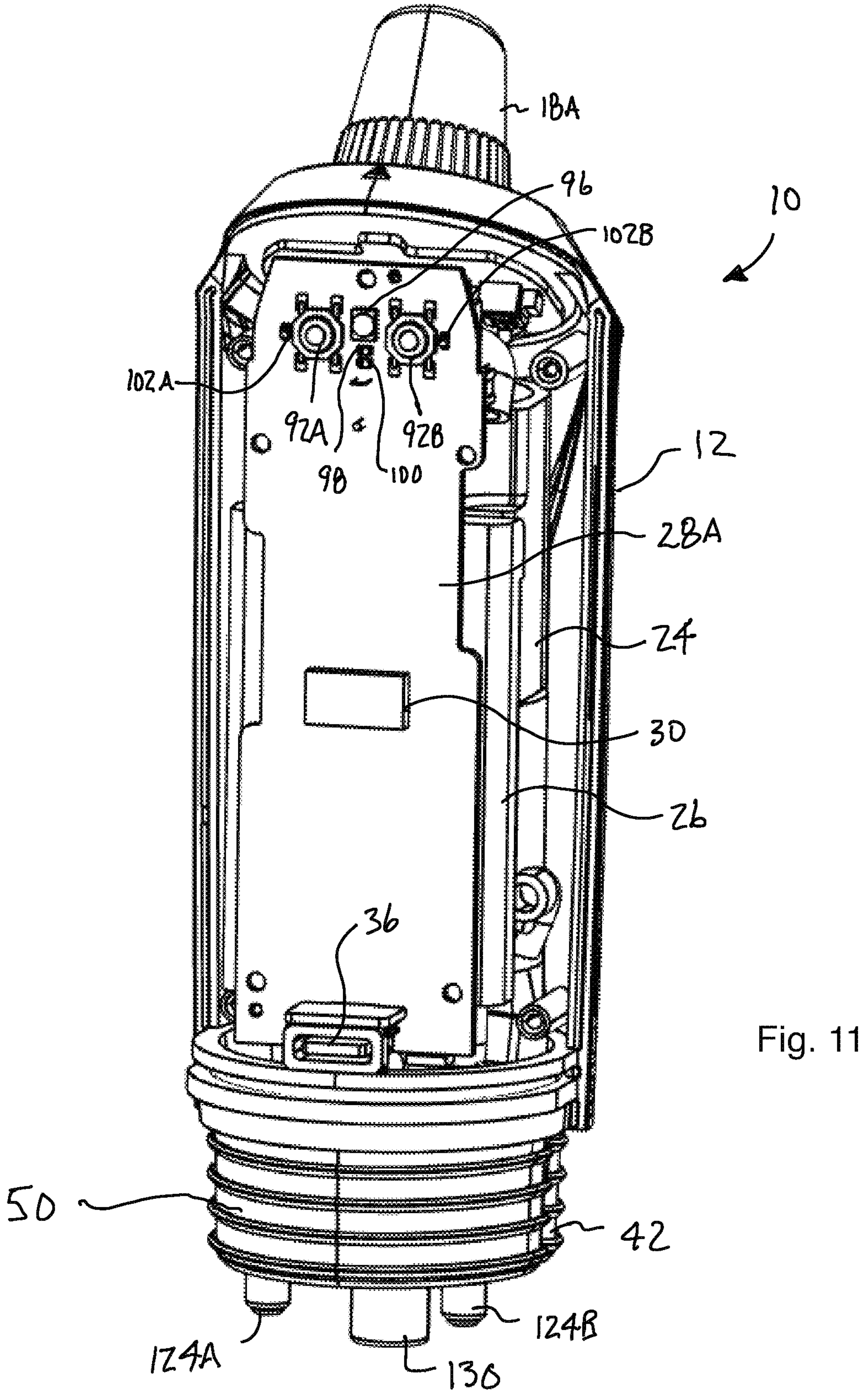
FIG. 11 is a second partially exploded perspective view of the main body with portions removed.

In the illustrated embodiment, the control system 22 includes a USB-C port 36. As shown in FIG. 10, the USB-C port 36 is mounted to the main PCB 28A and is accessible from outside of the device 10. In the illustrated embodiment, the USB-C port 36 is disposed within and accessible through an opening the housing 20. The device 10 may include a pliable, resilient cap 34 that is used to selectively close the USB-C port 36 when it is not in use. The cap 34 may be frictionally fitted into the USB-C port 36 and be configured to provide a generally leak-tight seal that reduces the chance of water or other foreign materials entering the USC port 36. The USB-C port 36 may be configured to supply power for charging the battery 26 and/or supplying power directly to the device 10. If desired, the USB-C port 36 may also be used to provide wired communication with the controller 22. For example, the device 10 may be configured so that the USB-C port 36 can be used to set device operating parameters, update software, firmware, acquire operating data that might be stored on the device 10. The USB-C port 36 may be replaced by one or more alternative electrical power or communications connectors. In some applications, the control system 22 may be configured with wireless communications, for example, through Wi-Fi, Bluetooth or other wireless protocols.

As noted above, the device 10 is configured to selectively provide red light therapy. The device 10 of the illustrated embodiment includes an array of red LEDs positioned at the working end of the device 10 that are configured to be selectively illuminated by the control system 22 to emit red light toward the skin when desired, for example, during massage mode. As perhaps best shown in FIG. 14, in the illustrated embodiment, the array of red LEDs includes four red LEDs 90 mounted to the head PCB 28B in spaced apart relation. The red LEDs 90 are positioned and oriented to emit red light toward any working attachment affixed to the device 10. In the illustrated embodiment, a diffuser sheet 122 is positioned over the red LEDs 90 to diffuse the red light emitted by the LEDs 90 and provide more uniform distribution of red light. In some applications, the diffuser sheet 122 may be eliminated or replaced by other structure capable of diffusing the red light. In the illustrated embodiment, the massage head 18C is manufactured from transparent or translucent material so that the red light is able to pass through the massage head 18C onto the skin. The translucency of the massage head 18C may be tuned to provide the desired level of diffusion. The control system 22 may be configured to activate the red LEDs whenever it is desirable to provide red light therapy. In one embodiment, the control system 22 is configured to automatically activate the red LEDS 90 when the device 10 is operated in massage mode. The red LEDs may be activated at other times, if desired. For example, in alternative applications, the red LEDs may be automatically activated during all modes of operation or the red LEDs may be manually activated and deactivated as desired by the user.

In the illustrated embodiment, the device 10 includes a user interface that allows the user to control operation of the device and allows the device 10 to provide information regarding operation of the device 10. The illustrated user interface is merely exemplary and the device 10 may be operated using a wide range of alternative user interfaces. In the illustrated embodiment, the user interface generally includes an input button 32, a pair of switched 92A and 92B and a plurality of LEDs. The illustrated button 32 inputs a flexible and resilient button cover 94 that overlies the two underlying switches 92A and 92B. The button cover 94 allows a user to manipulate the underlying switches 92A and 92B while providing a leak-tight seal. In the illustrated embodiment, a pair of button extensions 126A and 126B are situated between the button cover 94 and the underlying switches 92A and 92B, respectively. The illustrated button cover 94 is transparent or translucent so that light from the underlying LEDs is visible through the button cover 94, but it may be opaque in alternative applications. In the illustrated embodiment, the plurality of LEDs includes a central RGB LED 96 that can be illuminated to produce essentially any color, a central red LED 98 that can be illuminated to provide visible feedback, for example, when an error condition occurs (e.g. supply canister 14 is empty, waste receptacle 16 is full, the tip is not properly engaged with the skin and/or essentially any other error condition exists). Additionally or alternatively, the red LED 98 may be illuminated when the device is providing red light therapy (e.g. the red LEDs 90 in the head of the device are illuminated). The green LED 100 may be illuminated to provide a visible indication that the device 10 is operating properly. The white LEDs 102A and 102B may be operated to illuminated the button cover 94. It should be understood that the various LED illumination schemes set forth above are merely exemplary and that the control system 22 may be programmed to implement essentially any desired illumination scheme. For example, in the illustrated embodiment, the left half of the button 32 is configured to operate as the "Power" button and the right half of the button 32 is configured to operate as the "Massage" button. As noted above, depression of the left half of the button actuates switch 92A and depression of the right half of the button actuates switch 92B. The user can push the "Power" button (actuating switch 92A) to turn the device 10 on and off, and to cycle between the available suction levels. In this embodiment, the button 32 is illuminated with a white light when the device 10 is first powered on. The user may press and hold the "Power" button to turn off the device. Once the device is on, the user can press to the "Power" button to cycle through the three different suction levels available in hydradermabrasion mode. As noted above, the number of selectable suction levels may vary from application to application. In this embodiment, the color of the "Power" button will change with changes in the suction level. For example, in the illustrated embodiment, the "Power" button will illuminate in blue when in low suction mode, illuminate in yellow when in medium suction level and illuminate in pink when in high suction level. The colors used to designate the different color levels may vary from application. In some implementation, the user interface will not provide color variations associated with different suction levels. In the illustrated embodiment, the device 10 automatically begins operating at the selected level of suction. In the illustrated embodiment, the device, once started, will continue to operate in hydradermabrasion mode for a predetermined period of time. In alternative applications, the device may be configured to continue to operate until deactivated by the user and/or for a period of time selected by the user. To operate the device in massage mode, the user may turn the device on (as described above) and then press the "Massage" button (actuating switch 92B). The device 10 will then disable the pump and will activate the red LEDs located under the massage head 18C. The user can then use the device to massage and apply red light therapy to the target location. Once started, the device 10 will continue to operate in massage mode for a predetermined period of time. In alternative applications, the device may be configured to continue to operate in massage mode until deactivated by the user and/or for a period of time selected by the user.

General operation of the device 10 will now be described with reference to the drawings. As noted above, the device 10 of the illustrated embodiment is configured to selectively operate in hydradermabrasion mode or in massage mode. To prepare the device 10 to operate in hydradermabrasion mode, a hydradermabrasion tip 18A or 18B is installed on the device 10 by the user. More specifically, the stem receptacle 72A or 72B of the desired tip 18A or 18B is installed over the mounting stem 68 and the base 70A or 70B is fitted into the recess 66. To provide proper alignment, the tip 18A or 18B is oriented with the asymmetric feature 76 of the tip in alignment with the asymmetric feature 74 of the device 10. A supply canister 14 containing the desired liquid is mounted on the device 10. For example, in the illustrated embodiment, the mouth 40 of the supply canister 14 is fitted over the supply canister mounting seal 42 until it is firmly seated. The supply canister 14 may contain essentially any desired liquid, such as water or any other liquid that may be desirable for purposes of cleaning, hydrating, nourishing or otherwise treating or providing benefit to the skin. The plug 38 is fitted into the bottom end 48 of the waste receptacle 16 to close the waste receptacle 16 and prepare it to receive waste liquid and debris from the hydradermabrasion process. Once the device 10 is prepared for hydradermabrasion mode, the user may initiate hydradermabrasion using the user interface, for example, by entering the appropriate inputs using the buttons 32. The device 10 may provide feedback to the user by illuminating the LEDs, such as the RGB LED 98, the red LED 98 and/or the green LED 100, in a manner consistent with the user manual.

Figure 12:
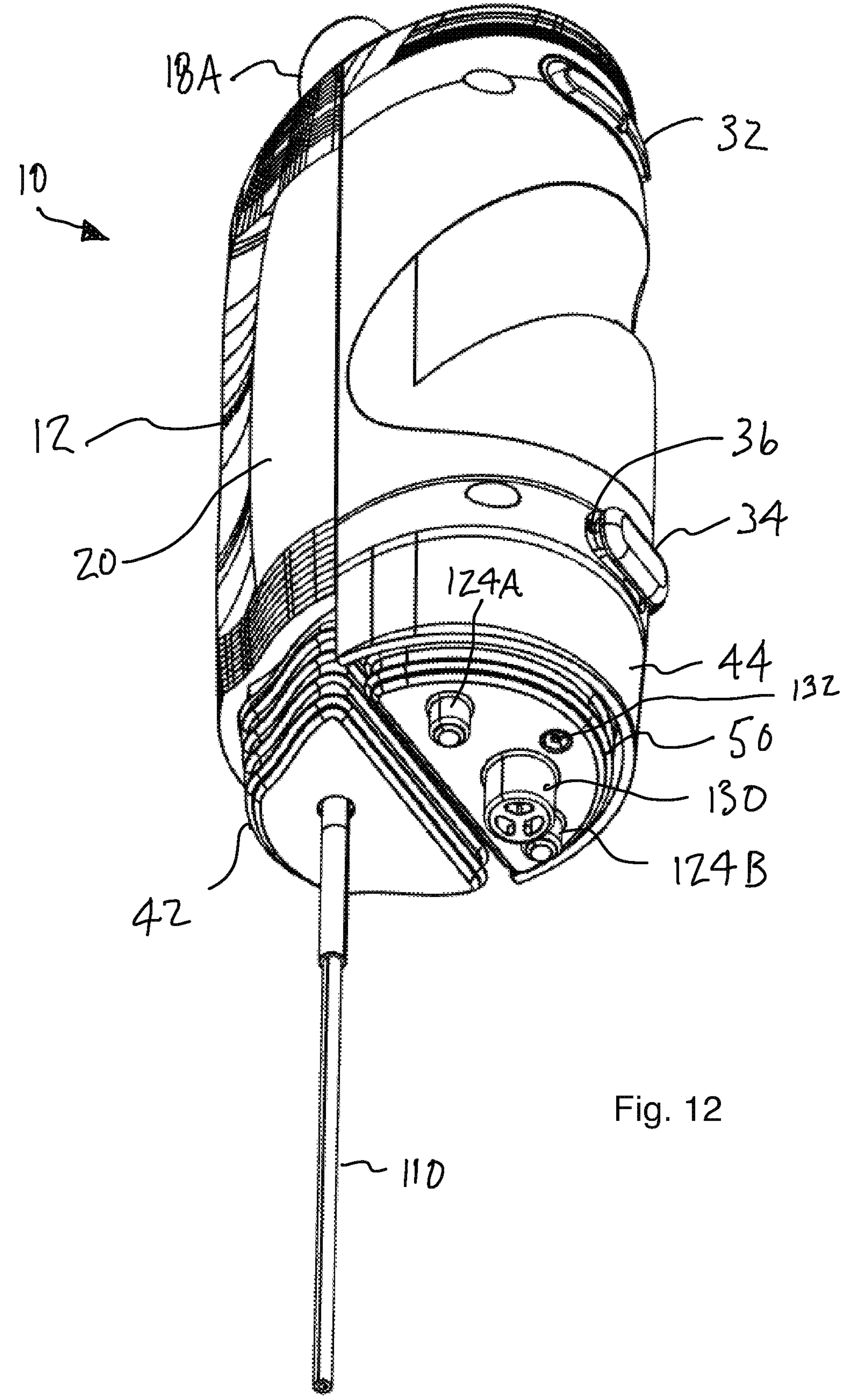
FIG. 12 is a bottom perspective view of the device with portions removed to show the underside of the main body.
Figure 13:
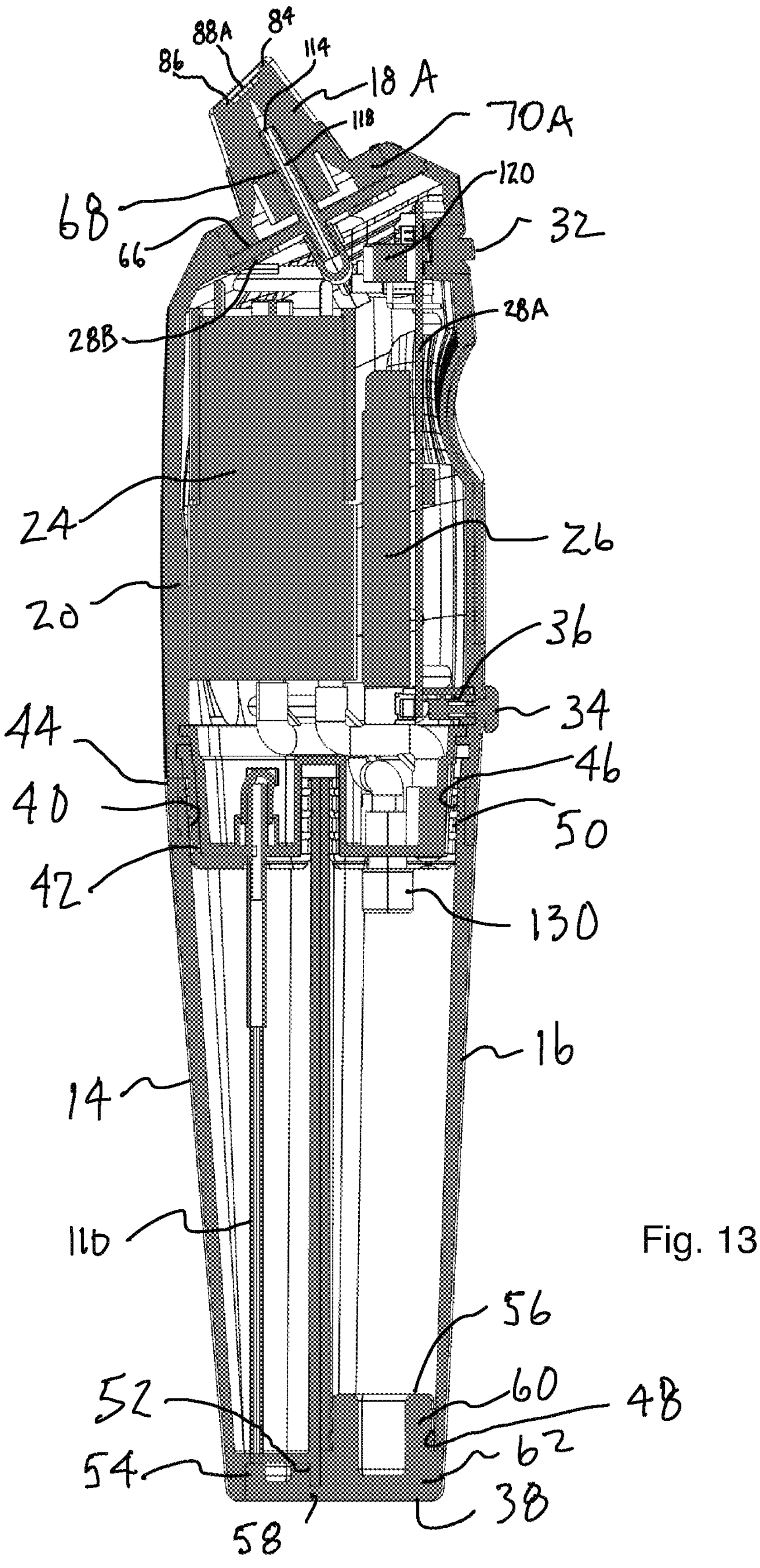
FIG. 13 is a sectional view of the device with the first tip installed.

Once the control system 22 is direct by the user to operate in hydradermabrasion mode, the controller 30 will activate the pump 24. Upon activation, the pump 24 begins to draw a partial vacuum in the waste receptacle 16 via the vacuum line 104. The vacuum line 104 opens into the waste receptacle 16 at vacuum inlet 132 (See FIG. 12). The partial vacuum in the waste receptacle 16 is communicated to the suction head of the tip 18A or 18B. More specifically, the partial vacuum is communicated through the return line 106 to the return passage 118 and return port 114 of the mounting stem 68, and in turn to the return through hole 80 in the tip 18A or 18B. This results in a partial vacuum being drawn in the inner region 86 of the suction head. The partial vacuum in the inner region 86 has the potential to draw air/liquid and debris away from the inner region 86 to the waste receptacle 16. It should be noted that when the suction head is not properly engaged with the skin, the inner region 86 is open to the environment, such that the partial vacuum draws air from the environment and no liquid is drawn from the supply canister 14. However, when the outer surface 82 of the tip 18A or 18B is closed by engagement with the user's skin (e.g. face), the partial vacuum from the waste receptacle 16 is communicated through the inner region 86 to the supply canister 14. This partial vacuum consequently draws liquid from the supply canister 14 to the inner region 86 of the suction head. More specifically, the partial vacuum in the inner region 86 is communicated through the supply through hole 78, the supply port 112, the supply passage 116, the supply line 108 and the supply tube 110 where it draws liquid from the supply canister 14. In the illustrated embodiment, liquid is drawn to inner region 86 with sufficient force for the liquid to jet into the skin to mechanically remove dead skill cells and other debris. As noted above, operation of the pump 24 may be varied to adjust the force of the jetting liquid and level of suction provided at the suction head. The liquid, dead skill cells and other debris are drawn away from the inner region 86 into the waste receptacle 16 where they are temporarily stored until emptied by the user.

In the illustrated embodiment, the waste receptacle 16 include a return inlet 130 through which waste moved through the return line 106 enters the waste receptacle 16. In this embodiment, the return inlet 130 includes a check valve that is configured to reduce the possibility of waste liquid flow back out of the waste receptacle 16, for example, when the device 10 is inverted. The check valve may be a one-way ball valve or it may be another type of check valve or flow control device that prevents flow of waste in the wrong direction. In some applications, the check valve may be eliminated.

In the illustrated embodiment, the control system 22 and orientation sensor 120 are configured to temporarily disable the pump 24 if the device 10 is tilted too far away from the desired orientation. For example, if the device 10 is positioned upside down, the open end of the supply tube 110 will no longer be positioned in liquid and the device 10 not function properly. As a result, the control system 22 is configured to disable the pump 24 when the device 10 is not within the proper orientation window, and to reactivate the pump 24 when the device 10 is returned to an acceptable orientation. The control system 22 may be configured to provide a visual and/or audible signal when the device 10 is outside an acceptable orientation window. The control system 22 may be configured to automatically reactivate the pump 24 or it may be configured to require manual reactivation by the user. In the illustrated embodiment, the pump 24 is deactivated when the device 10 is outside the following orientation range: Front: about 85°; Rear: about 35°; Left and Right: about 60°, but the ranges may vary from application to application as desired. For example, in some alternative applications, one or more of these orientation values may be varied by ±10°.

In the illustrated embodiment, the control system 22 and the level sensor 124 are configured to temporarily disable the pump 24 when the waste receptacle 16 is full. As noted above, the level sensor 124 includes two pins 124A and 124B that are spaced apart from one another inside the waste receptacle 16 near its top end. When the waste receptacle 16 is full enough for the waste liquid to reach the two pins 124A and 124B, the liquid will create an electrically-conductive bridge between the two pins 124A and 124B that can be sensed by the level sensor 124 or by the controller 30. When this condition is sensed, the controller 30 will disable the pump 24 until the liquid level drops, for example, as a result of the user emptying the waste receptacle 16 by removing plug 38 and allowing the contents to spill into a sink or other receptacle. The control system 22 may be configured to provide a visual and/or audible signal when the waste receptacle 16 is full. The control system 22 may be configured to automatically reactivate the pump 24 when the waste receptacle 16 is emptied or it may be configured to require manual reactivation by the user.

The device 10 may be provided with different tips, such as tips 18A or 18B, that are designed to treat different skin regions or that are designed to provide different types of hydradermabrasion. For example, a tip with a smaller suction head may be provided for regions of the skin that have significant contour, while a tip with a larger suction head may be provide for regions with less contour. As another example, different tips may be provided with through holes (e.g. through holes 78 and 80) that vary in number, size, location or other characteristics to vary the hydradermabrasion provided by each tip.

As noted above, the device 10 is also configured to operate in massage mode. In massage made, the device 10 of the illustrated embodiment provides red light therapy, but does not circulate any liquid. To prepare the device 10 for massage mode, the massage head 18C is fitted to the device 10 by the user. More specifically, the stem receptacle 72C of the massage head 18C is installed over the mounting stem 68 and the base 70C is fitted into the recess 66. To provide proper alignment, the massage head 18C is oriented with the asymmetric feature of the tip 76 in alignment with the asymmetric feature 74 of the device 10. If desired, a massaging lotion, oil or other material may be applied to the outer surface of the massage head 18C or directly to the skin to be massaged. Given that no liquid will be circulated during massage mode, it is unnecessary to fill the supply canister 14 with liquid or to address the "fill status" of the waste receptacle 16.

Once the device 10 is prepared for massage mode, the user may initiate massage mode using the user interface, for example, by entering the appropriate inputs using the buttons 32. The device 10 may provide feedback to the user by illuminating the LEDs, such as the RGB LED 98, the red LED 98 and/or the green LED 100, in a manner consistent with the user manual. Once massage mode is initiated, the control system 22 of the illustrated embodiment will illuminate the red LEDs 90 situated under the massage head 18C. The light from the red LEDs 90 will pass through the diffuser sheet 122 and the transparent or translucent massage head 18C onto the skin being massaged. The device 10 may be operated in massage mode until the desired massage therapy is complete. In some applications, a serum, lotion, oil and/or other topical agent may be applied to the target area and massaged into the skin using the massage head 18C.

Although the different elements and assemblies of the embodiments are described herein as having certain functional characteristics, each element and/or its relation to other elements can be depicted or oriented in a variety of different aesthetic configurations, which support the ornamental and aesthetic aspects of the same. Simply because an apparatus, element or assembly of one or more of elements is described herein as having a function does not mean its orientation, layout or configuration is not purely aesthetic and ornamental in nature.

Directional terms, such as "vertical," "horizontal," "top," "bottom," "upper," "lower," "inner," "inwardly," "outer" and "outwardly," are used to assist in describing the invention based on the orientation of the embodiments shown in the illustrations. The use of directional terms should not be interpreted to limit the invention to any specific orientation(s).

In addition, when a component, part or layer is referred to as being "joined with," "on," "engaged with," "adhered to," "secured to," or "coupled to" another component, part or layer, it may be directly joined with, on, engaged with, adhered to, secured to, or coupled to the other component, part or layer, or any number of intervening components, parts or layers may be present. In contrast, when an element is referred to as being "directly joined with," "directly on," "directly engaged with," "directly adhered to," "directly secured to," or "directly coupled to" another element or layer, there may be no intervening elements or layers present. Other words used to describe the relationship between components, layers and parts should be interpreted in a like manner, such as "adjacent" versus "directly adjacent" and similar words. As used herein, the term "and/or" includes any and all combinations of one or more of the associated listed items.

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular. Any reference to claim elements as "at least one of X, Y and Z" is meant to include any one of X, Y or Z individually, any combination of X, Y and Z, for example, X, Y, Z; X, Y; X, Z; Y, Z, and/or any other possible combination together or alone of those elements, noting that the same is open ended and can include other elements.

What is claimed is:

1. A skin treatment device comprising:

a main body having a working end with a mount configured to removably receive a working attachment;

a supply canister removably affixed to the main body and oriented to extend along a longitudinal axis of the main body, the supply canister includes a reservoir configured to retain a liquid;

a waste receptacle affixed to a distal portion of the main body within a handle portion thereof in fluid communication with the working end, the waste receptacle including a plug for selectively opening and closing the waste receptacle;

a liquid delivery system for moving liquid from the supply canister to a working attachment and from the working attachment to the waste receptacle;

a plurality of interchangeable working attachments, each of the plurality of interchangeable working attachments being configured to selectively mount to the working end of the main body, the plurality of working attachments including at least one hydradermabrasion tip and at least one massage head, the at least one hydradermabrasion tip having a supply aperture through which the liquid is delivered to a target surface and a return aperture through which the liquid is moved from a target surface to the waste receptacle;

a control system operatively coupled to the liquid delivery system; and an orientation sensor operatively coupled to the control system, wherein the control system is configured to adjust operation of the liquid delivery system based on data received from the orientation sensor.

2. The device of claim 1 further comprising a red light therapy system, the red light therapy system including one or more red light sources to produce red light, the one or more red light sources being disposed toward the working end of the main body and configured to emit red light onto at least one of the plurality of working attachments mounted to the main body; and wherein the at least one massage head is translucent or transparent to allow the red light emitted by the one or more red light sources to reach a target surface.

3. The device of claim 2 wherein the one or more red light sources includes four red LEDs disposed adjacent the mount.

4. The device of claim 2 wherein the red light therapy system includes a diffuser sheet disposed between the one or more red light sources and at least one of the working attachments, the diffuser sheet diffusing the red light reaching at least one of the working attachments.

5. The device of claim 1 wherein the main body includes a housing and a structural seal protruding from the housing, the supply canister including a mouth, the mouth being removably fitted over the protruding structural seal, the structural seal providing a leak-tight seal with the supply canister.

6. The device of claim 1 wherein the control system is further configured to operate the device in hydradermabrasion mode and in massage mode, the control system configured to activate the liquid delivery system when operating in hydradermabrasion mode, and configured to deactivate the liquid delivery system when the device is outside of an acceptable orientation range.

7. The device of claim 6 wherein the control system further includes a waste receptacle liquid level sensor, the control system configured to deactivate the liquid delivery system as a function of the liquid level sensor.

8. The device of claim 7 wherein the mount includes a mounting stem with a supply through hole and a return through hole.

9. The device of claim 8 wherein the mount includes an asymmetric feature and the at least one hydradermabrasion tip includes an asymmetric feature, wherein the asymmetric feature of the mount and the asymmetric feature of the at least one hydradermabrasion tip are configured to mate to provide proper alignment between the mount and the hydradermabrasion tip.

10. The device of claim 9 wherein the liquid delivery system includes a pump in communication with the waste receptacle, the pump configured to selectively draw a partial vacuum within the waste receptacle.

11. A skin treatment system comprising:

a main body having a housing with a working end, the working end having a mount configured to receive a working attachment;

a hydradermabrasion working attachment removably mounted to the mount;

a supply canister having an interior configured to contain a supply liquid to be delivered via the hydradermabrasion working attachment to a target region, the supply canister being removably attached to a proximal portion of the main body and oriented to extend along a longitudinal axis of the main body;

a waste receptacle having an interior configured to contain a waste liquid returned from a target region via the hydradermabrasion working attachment, the waste receptacle being affixed to a distal portion of the main body within a handle portion thereof, and having a removable plug selectively removable to empty waste liquid from the interior of the waste receptacle; and a liquid delivery system having a pump and a plurality of flow lines, the plurality of flow lines including a vacuum line connecting the pump and the interior of the waste receptacle, a return line connecting the interior of the waste receptacle and the hydradermabrasion working attachment, a supply line connecting the hydradermabrasion working attachment and the interior of the supply canister;

a control system operatively coupled to the liquid delivery system; and an orientation sensor operatively coupled to the control system, wherein the control system is configured to adjust operation of the liquid delivery system based on orientation data.

12. The device of claim 11 further including a massage working attachment, the massage working attachment configured to be interchangeably mounted to the mount in place of the hydradermabrasion working attachment.

13. The device of claim 12 further including a red light therapy system, the red light therapy system including at least one red light source disposed adjacent the working end of the device, the massage working attachment being transparent or translucent, wherein red light emitted by the at least one red light source passes through the massage working attachment to a target area, whereby the device is capable of providing red light therapy to a target area that is being treated to a massage by the massage working attachment.

14. The device of claim 13 wherein the mount includes a mounting stem having a supply passage and a return passage, the supply line being operatively connected to the supply passage, the return line being operatively connected to the return passage.

15. The device of claim 14 wherein the red light therapy system includes a printed circuit board disposed adjacent to the mounting stem and a plurality of red LEDs disposed on the printed circuit board.

16. The device of claim 15 wherein the red light therapy system includes a diffuser sheet disposed over the red LEDs to diffuse red light emitted by the red LEDs.

17. The device of claim 11 wherein the main body includes a pair of structural seals protruding from the housing, the supply canister including a mouth, the supply canister mouth being removably fitted over a first of the protruding structural seals, the first structural seal providing a leak-tight seal with the supply canister, the waste receptacle including a mouth, the waste receptacle mouth being fitted over a second of the protruding structural seals, the second structural seal providing a leak-tight seal with the waste receptacle.

18. The device of claim 11 further including a control system configured to alternately operate the device in hydradermabrasion mode or in massage mode, the control system configured to activate the liquid delivery system when operating in hydradermabrasion mode, the control system having an orientation sensor and configured to deactivate the liquid delivery system when the device is outside of an acceptable orientation range.

19. The device of claim 18 wherein control system further includes a waste receptacle liquid level sensor, the control system configured to deactivate the liquid delivery system as a function of the liquid level sensor.

20. The device of claim 11 wherein the mount includes an asymmetric feature, the hydradermabrasion working attachment includes an asymmetric feature, wherein the asymmetric feature of the mount and the asymmetric feature of the hydradermabrasion working attachment are configured to mate to provide proper alignment between the mount and the hydradermabrasion working attachment.

21. A method of using a skin treatment device, the method comprising:

providing a skin treatment device with a main body having a mount and a plurality of working attachments interchangeably mountable to the mount, the plurality of working attachments including at least one hydradermabrasion tip and at least one massage head, the skin treatment device including a liquid delivery system, a red light therapy system, a control system operatively coupled to the liquid delivery system, a supply canister removably affixed to a proximal portion of the main body, and a waste receptacle integrated into a distal portion of the main body within a handle portion thereof, the waste receptacle including a plug for selectively opening and closing the waste receptacle;

mounting a hydradermabrasion tip on the mount;

providing the supply canister containing a supply liquid be delivered to a region of skin;

performing hydradermabrasion on a region of skin by operating the device in a hydradermabrasion mode with the liquid delivery system moving supply liquid from the supply canister to a region of skin via the hydradermabrasion tip and from the region of skin to the waste receptacle via the hydradermabrasion tip;

removing the hydradermabrasion tip from the mount;

mounting a massage head on the mount; and performing massage on a region of skin by moving the massage head over a region of skin while operating the red light therapy system to produce red light that passes through the massage head to a region of skin.

22. The method of claim 21 further comprising the step of emptying the waste receptacle by removing a removable plug from the waste receptacle while the waste receptacle remains attached to the main body.

23. The method of claim 22 wherein the skin treatment device includes a control system with an orientation sensor; and further comprising the step of selectively deactivating the liquid delivery system when the control system determines that the device is outside of a predetermined orientation range based on the orientation sensor.

24. The method of claim 23 wherein the skin treatment device includes a waste receptacle level sensor; and further comprising the step of selectively deactivating the liquid delivery system when the control system determines that the waste receptacle is full based on the waste receptacle level sensor.

* * * * *